(12) United States Patent
Christensen

(10) Patent No.: US 6,875,242 B2
(45) Date of Patent: Apr. 5, 2005

(54) PROSTHETIC FOOT WITH ENERGY TRANSFER MEDIUM INCLUDING VARIABLE VISCOSITY FLUID

(75) Inventor: Roland J. Christensen, Fayette, UT (US)

(73) Assignee: Roland J. Christensen, as operating Manager of RJC Development, LC, General Partner of the Roland J. Christensen Family Limited Partnership, Fayette, UT (US)

(*) Notice: Subject to any disclaimer, the term of this patent is extended or adjusted under 35 U.S.C. 154(b) by 0 days.

(21) Appl. No.: 10/738,645

(22) Filed: Dec. 16, 2003

(65) Prior Publication Data

US 2004/0133284 A1 Jul. 8, 2004

Related U.S. Application Data

(63) Continuation of application No. 10/137,933, filed on May 3, 2002, now Pat. No. 6,663,673, which is a continuation-in-part of application No. 09/607,494, filed on Jun. 30, 2000, now abandoned.

(51) Int. Cl.[7] .................................................. A61F 2/66
(52) U.S. Cl. ...................................................... 623/56
(58) Field of Search ............................... 623/24, 36, 37, 623/49, 53, 55, 56, 54

(56) References Cited

U.S. PATENT DOCUMENTS

| | | | |
|---|---|---|---|
| 42,799 A | 5/1864 | Shepard |
| 92,031 A | 6/1869 | Foster |
| 292,800 A | 2/1884 | Furrer |
| 497,026 A | 5/1893 | Judson |
| 1,001,641 A | 8/1911 | Harrison |
| 1,779,765 A | 10/1930 | Eichhorn |
| 1,996,874 A | 4/1935 | Mascau |
| 2,036,830 A | 4/1936 | Rowley |
| 2,379,538 A | 7/1945 | Meierhofer |
| 2,443,356 A | 6/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 11/1953 | Wisbrun |
| 2,843,853 A | 6/1958 | Mauch |
| 3,548,420 A | 12/1970 | Spence |
| 3,551,914 A | 1/1971 | Woodall |
| 3,858,379 A | 1/1975 | Graves et al. |
| 3,871,032 A | 3/1975 | Karas |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,506,395 A | 3/1985 | Haupt |
| 4,547,913 A | 10/1985 | Phillips |
| 4,606,332 A | 8/1986 | Gibson |
| 4,645,509 A | 2/1987 | Poggi et al. |
| 4,676,801 A | 6/1987 | Lundeen |
| 4,721,510 A | 1/1988 | Cooper et al. |

(Continued)

*Primary Examiner*—Bruce E Snow
(74) *Attorney, Agent, or Firm*—Thorpe North & Western

(57) ABSTRACT

A device prosthetic foot device with variable stiffness response includes a variable energy transfer medium disposed between first and second foot members to transfer at least some energy from the second member to the first member during use. The energy transfer medium includes a variable viscosity fluid such that the variable viscosity fluid, and thus the energy transfer medium, variably transfers energy between the first and second members to vary stiffness of the prosthetic foot device. The variable viscosity fluid can include a shear stiffening material that increases in viscosity as a load or strain, or rate of loading or rate of strain, applied, or a magneto or electro rheologic fluid responsive to a magnetic or electric field.

11 Claims, 7 Drawing Sheets

U.S. PATENT DOCUMENTS

| | | |
|---|---|---|
| 4,822,363 A | 4/1989 | Phillips |
| 4,865,611 A | 9/1989 | Al-Turaiki |
| 4,938,775 A | 7/1990 | Morgan |
| 4,959,073 A | 9/1990 | Merlette |
| 5,019,109 A | 5/1991 | Voisin |
| 5,030,239 A | 7/1991 | Copes |
| 5,037,444 A | 8/1991 | Phillips |
| 5,112,356 A | 5/1992 | Harris et al. |
| 5,116,383 A | 5/1992 | Shorter et al. |
| 5,116,384 A | 5/1992 | Wilson et al. |
| 5,181,932 A | 1/1993 | Phillips |
| 5,181,933 A | 1/1993 | Phillips |
| 5,217,500 A | 6/1993 | Phillips |
| 5,290,319 A | 3/1994 | Phillips |
| 5,376,133 A | 12/1994 | Grammes |
| 5,376,141 A | 12/1994 | Phillips |
| 5,387,246 A | 2/1995 | Phillips |
| 5,425,781 A | 6/1995 | Allard et al. |
| 5,425,782 A | 6/1995 | Phillips |
| 5,443,528 A | 8/1995 | Allen |
| 5,443,529 A | 8/1995 | Phillips |
| 5,458,656 A | 10/1995 | Phillips |
| 5,464,441 A | 11/1995 | Phillips |
| 5,482,513 A | 1/1996 | Wilson |
| 5,486,209 A | 1/1996 | Phillips |
| 5,507,838 A | 4/1996 | Chen |
| 5,509,936 A | 4/1996 | Rappoport et al. |
| 5,509,938 A | 4/1996 | Phillips |
| 5,514,185 A | 5/1996 | Phillips |
| 5,514,186 A | 5/1996 | Phillips |
| 5,549,714 A | 8/1996 | Phillips |
| 5,571,210 A | 11/1996 | Lindh |
| 5,571,213 A | 11/1996 | Allen |
| 5,593,455 A | 1/1997 | Phillips |
| 5,593,456 A | 1/1997 | Merlette |
| 5,593,457 A | 1/1997 | Phillips |
| 5,653,767 A | 8/1997 | Allen et al. |
| 5,725,598 A | 3/1998 | Phillips |
| 5,728,175 A | 3/1998 | Rincoe |
| 5,728,176 A | 3/1998 | Phillips |
| 5,728,177 A | 3/1998 | Phillips |
| 5,766,265 A | 6/1998 | Phillips |
| 5,769,896 A | 6/1998 | Rosendahl et al. |
| 5,776,205 A | 7/1998 | Phillips |
| 5,779,735 A | 7/1998 | Molino |
| 5,800,565 A | 9/1998 | Biedermann |
| 5,800,569 A | 9/1998 | Phillips |
| 5,824,112 A | 10/1998 | Phillips |
| 5,888,238 A | 3/1999 | Phillips et al. |
| 5,893,891 A | 4/1999 | Zahedi |
| 5,899,944 A | 5/1999 | Phillips |
| 5,976,191 A | 11/1999 | Phillips |
| 5,993,488 A | 11/1999 | Phillips |
| 6,019,795 A | 2/2000 | Phillips |
| 6,071,313 A | 6/2000 | Phillips |
| 6,165,227 A | 12/2000 | Phillips |
| 6,206,934 B1 | 3/2001 | Phillips |
| 6,254,643 B1 | 7/2001 | Phillips |
| 6,261,324 B1 | 7/2001 | Merlette |
| 6,280,479 B1 | 8/2001 | Phillips |
| 6,290,730 B1 | 9/2001 | Pitkin et al. |
| 6,443,993 B1 | 9/2002 | Koniuk |

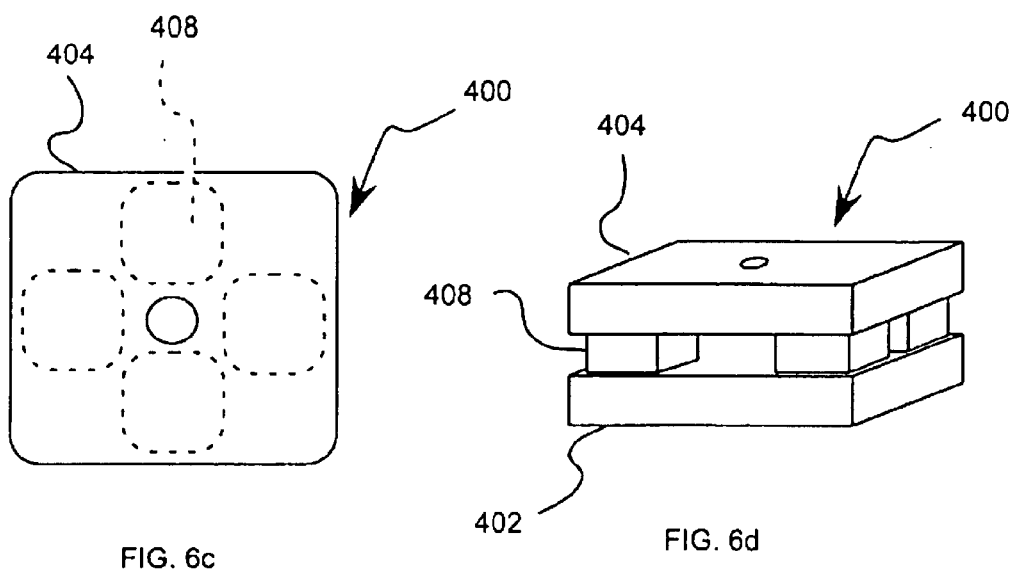
FIG. 6c
FIG. 6d
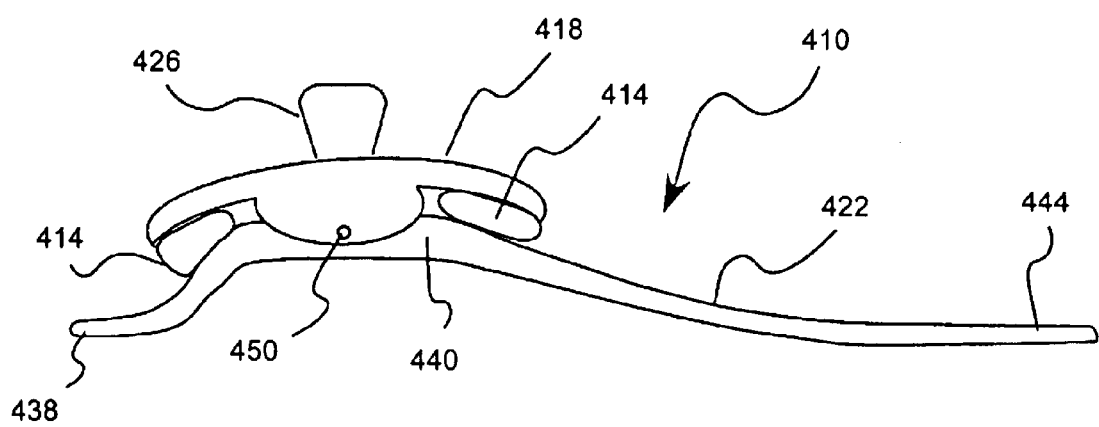
FIG. 7

PROSTHETIC FOOT WITH ENERGY TRANSFER MEDIUM INCLUDING VARIABLE VISCOSITY FLUID

This application is a continuation of U.S. patent application Ser. No. 10/137,933, filed May 03, 2002, now U.S. Pat. No. 6,663,673, which is a continuation-in-part of U.S. application Ser. No. 09/607,494, filed Jun. 30, 2000, now abandoned.

BACKGROUND OF THE INVENTION

1. Field of the Invention

The present invention relates generally to prosthetic feet. More particularly, the present invention relates to prosthetic feet with an energy transfer medium including a variable viscosity fluid.

2. Related Art

Many individuals have lost a limb for various reasons including war, accident, or disease. In most instances, these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward. Examples of such energy storing, spring-like feet include U.S. Pat. Nos. 5,037,444; 4,547,913; 5,181,932 and 5,976,191.

The prosthetic feet typically include spring-like members that are typically flexible and resilient. In order to provide a natural feel and cushion of a natural foot, the members must be flexible and deflect under the user's weight. Such flexibility and the ability to deflect often require the members forming the foot to be structurally weak, or more flexible. On the other hand, it is desirable to make the members as strong or stiff as possible from a structural and durability standpoint. Thus, there may be a trade-off between obtaining a sufficient cushion or feel, with members that are weak or flexible and over-deflect, and obtaining a solid and durable structural foot, with stiffer members.

The stiffness of prosthetic feet typically varies according to the intended use. Feet intended for everyday use typically require a soft feel, and thus incorporate a softer spring. Feet intended for athletic use typically require strength, and thus incorporate a stiff spring. Feet designed for particular purposes are typically unsuited for other purposes. Stiff, athletic feet are too hard for everyday use, and soft, everyday feet are too fragile for athletic use. Multiple-use feet have been designed which are capable of many different uses, but without being particularly well suited for any specialized use.

In addition, users may have different weights. Thus, prosthetic feet may require a high degree of custom design, or be particularly tailored to the individual user. However, it is desirable from a cost and manufacturing standpoint to create a foot that is usable by many sizes of individuals.

SUMMARY OF THE INVENTION

It has been recognized that it would be advantageous to develop a prosthetic foot with adjustable stiffness for accommodating different uses or different users.

The invention provides a prosthetic foot device with variable stiffness response with a variable energy transfer medium disposed between first and second members. The first member can be coupled to an amputee, while the second member can be coupled to the first member, and can operate between the first member and ground during use. The variable energy transfer medium transfers at least some energy from the second member to the first member during use. The energy transfer medium advantageously includes a variable viscosity fluid such that the variable viscosity fluid, and thus the energy transfer medium, variably transfers energy between the first and second members to vary stiffness of the prosthetic foot device.

In accordance with a more detailed aspect of the present invention, the first and/or second members can include a resilient member capable of storing energy during deflection.

In accordance with another more detailed aspect of the present invention, the variable viscosity fluid can include a shear stiffening material that increases in viscosity as a load or strain, or load rate or strain rate, applied to the shear stiffening material by the second member increases.

In accordance with another more detailed aspect of the present invention, the variable viscosity fluid can include a magneto or electro rheologic fluid responsive to a magnetic or electric field. A transducer can be coupled to the first and/or second member to sense a load factor in the member or foot device. A power source and control electronics can be coupled to the transducer and the variable viscosity fluid to apply the magnetic or electric field in response to the load factor sensed by the transducer.

In accordance with another more detailed aspect of the present invention, the first member can include an upper member having an attachment section to be coupled to a socket, and extending downwardly therefrom. The second member can include a lower foot member having a heel section disposed at a natural location of a heel of a user, and a toe section disposed at a natural location of a toe of the user.

In accordance with another more detailed aspect of the present invention, the first member can include an upper forefoot member having an attachment section to be coupled to a socket, and extending downwardly therefrom. The second member can include a lower heel member having a heel section disposed at a natural location of a heel of a user, and an attachment section attached to the upper forefoot member.

In accordance with another more detailed aspect of the present invention, the first member can include both 1) an upper forefoot member having an attachment section to be coupled to a socket, and extending downwardly therefrom, and 2) a lower heel member having a heel section disposed at a natural location of a heel of a user, and an attachment section attached to the upper forefoot member. The second member can include a forefoot reinforcement member and/or a heel reinforcement member. The forefoot reinforcement member can be disposed above the upper forefoot member, while the heel reinforcement member can be disposed above the lower heel member.

In accordance with another more detailed aspect of the present invention, the first member can be an adaptor, while the second member can be a prosthetic foot. The second member can include at least an upper member having an attachment section attached to the adaptor and configured to be coupled to the socket by the adaptor, and extending downwardly therefrom.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 6c is a partial top view of another prosthetic foot having an energy transfer medium with variable viscosity fluid in accordance with another embodiment of the present invention;

FIG. 6d is a partial perspective view of another prosthetic foot having an energy transfer medium with variable viscosity fluid in accordance with another embodiment of the present invention; and FIG. 7 is a side view of another prosthetic foot having an energy transfer medium with variable viscosity fluid in accordance with another embodiment of the present invention.

DETAILED DESCRIPTION

Figure 1:
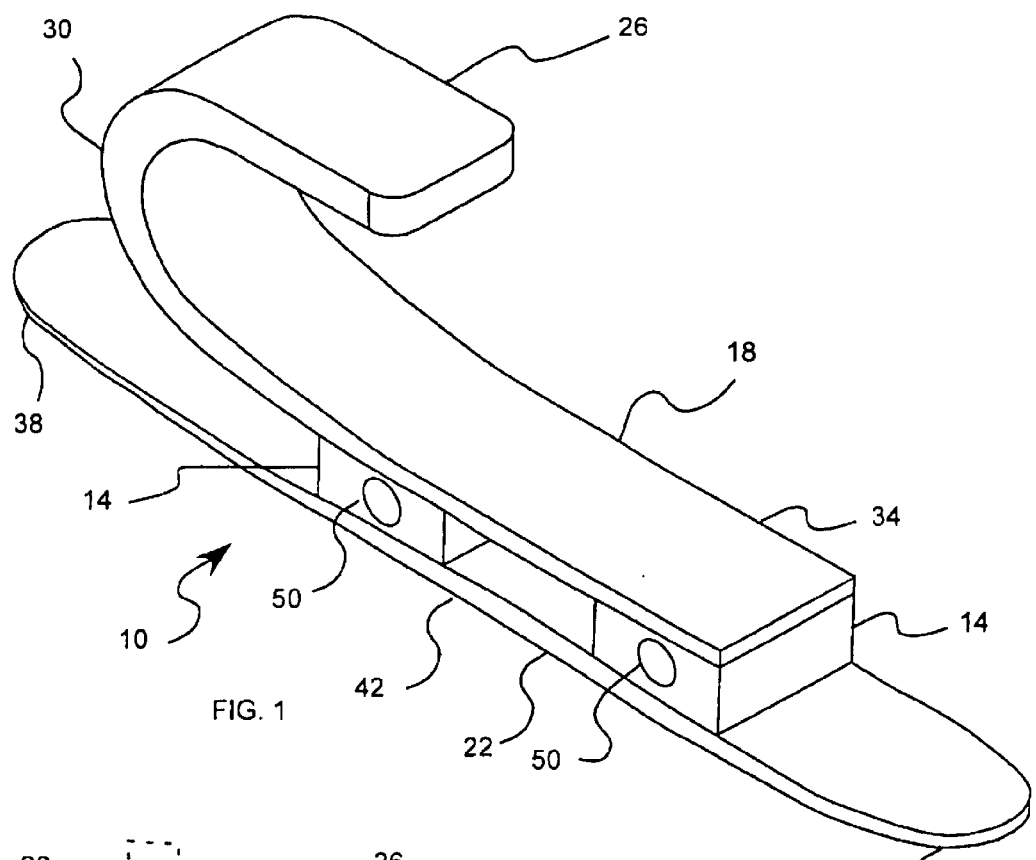
FIG. 1 is a perspective view of a prosthetic foot having an energy transfer medium with a variable viscosity fluid in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in the figures, various embodiments of prosthetic feet in accordance with the present invention are shown with an energy transfer medium that advantageously includes a variable viscosity fluid or material. The energy transfer medium, or variable viscosity fluid or material, is located between first and second members of the foot so that energy is transferred between the first and second member, and thus through the energy transfer medium, during use. The variable viscosity of the fluid or material advantageously allows the energy transferred between the members to be varied, thus varying the stiffness or response of the foot. The variable viscosity fluid can increase in viscosity with an increase in a load factor applied to the variable viscosity fluid. Such load factors can include a load, a load rate, a strain, a strain rate, a pressure, a deflection, etc. As described in greater detail below, the variable viscosity fluid or material can include a shear stiffening material that increases in viscosity as load or strain, or load rate or strain rate, is applied; an electro rheologic fluid that changes viscosity under an applied electric field; or a magneto rheologic fluid that changes viscosity under an applied magnetic field.

As illustrated in FIG. 1, a prosthetic foot device, indicated generally at 10, in accordance with the present invention is shown with a variable energy transfer medium 14 for varying the stiffness or response of the foot device 10. As described above, the foot device 10 includes first and second members 18 and 22. The first member 18 is coupled to a stump of an amputee as is understood in the art, while the second member 22 is coupled to the first member 18, and positioned to operate between the first member and the ground. The first member 18 can be sized and shaped as a forefoot or upper foot member that extends from an attachment portion 26, which is coupled to a stump of an amputee, downwardly and forwardly through an arcuate portion 30, to a coupling section 34 coupled to the second member 22. The second member 22 can be sized and shaped as a full-length sole or lower foot member that extends from a heel portion 38, through a coupling section 42 coupled to the first member 18, to a toe portion 44. It is believed that the configuration of the second member 22 as a full-length lower foot member provides a smoother gait.

The attachment portion 26 of the first member 18 can attach to a socket for receiving the stump of the amputee, as is known in the art. The socket is configured for the specific needs of the amputee, but typically has a portion adapted for standard attachment. The attachment portion 26 can be attached to the socket by any means, such as by nut and bolt, again as is known in the art. The first member 18 can be curved in a general C-shape, with the socket attaching to a top of the attachment portion 26 forming a horizontal attachment. Alternatively, a first member can be curved in a general L-shape or a J-shape, with the socket attaching to the side of the attachment portion forming a vertical attachment, as shown in dashed lines in FIG. 2.

The heel portion 38 of the second member 22 can be located at a heel location in a region near the rear of the foot device 10 where the heel of a natural foot would be located. Similarly, the toe portion 44 is located at a toe location in a region near the front of the foot device 10 where the toes of a natural foot would be located.

The first and second members 18 and 22 can be resilient and energy storing foot members that deflect or flex, storing energy, much like a leaf spring. Thus, the first and second members 18 and 22 can be formed of a flexible and resilient material that allows the foot members to deflect or flex. In one aspect, the members 18 and 22 can be formed of a fiber reinforced resin material, such as a graphite-reinforced resin.

The first member 18 can be disposed above, and spaced-apart from, the second member 22, such that the members 18 and 22 are in a non-contacting relationship, or are not directly attached. The energy transfer medium 14 can be disposed between, and can separate, the members 18 and 22. The energy transfer medium 14 can be more flexible than the energy-storing members 18 and 22, and allows the members 18 and 22 to move with respect to one another. In addition, the energy transfer medium 14 allows the members 18 and 22 to deflect or flex, and allows a greater range of motion of the members. The energy transfer medium 14 can include a resilient and compliant material, such as rubber or urethane. Thus, the energy transfer medium 14 can provide a cushioned, softer, and less stiff feel to the foot device 10, making the foot device more comfortable and natural. The addition of the energy transfer medium 14 also advantageously allows the first and second members 18 and 22 to be stiffer and stronger, while still providing a softer, cushioned feel. Thus, the stiffer stronger members 18 and 22 can be more durable. Various aspects of a prosthetic foot with an energy transfer medium are disclosed in U.S. patent application Ser. No. 09/607,494, which is herein incorporated by reference.

Figure 2:
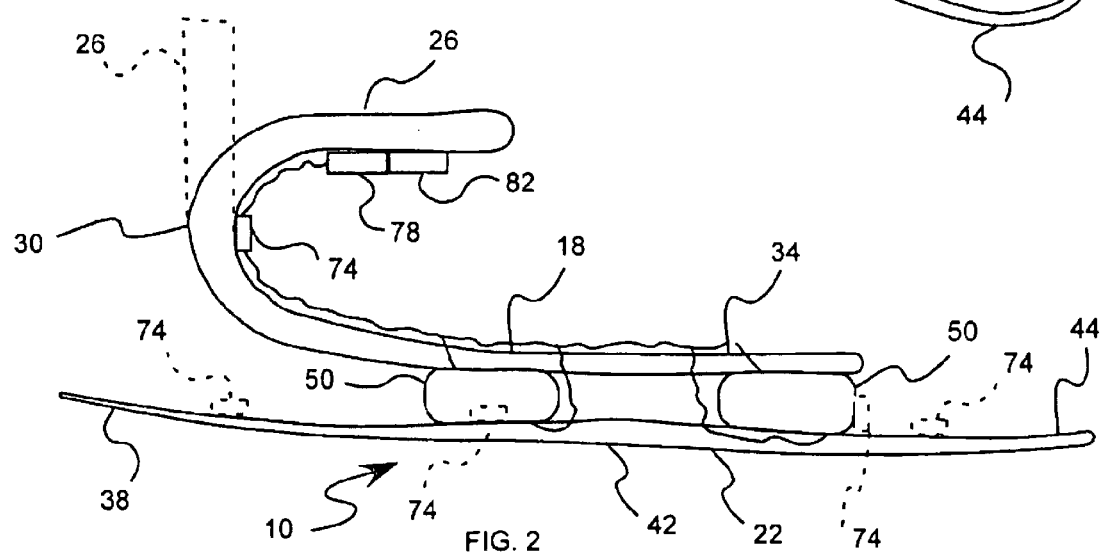
FIG. 2 is a side view of another prosthetic foot having an energy transfer medium with variable viscosity fluid in accordance with another embodiment of the present invention.

The energy transfer medium 14 also advantageously includes a variable viscosity fluid or material 50. The variable viscosity fluid 50 can be included in pockets or cavities formed in the energy transfer medium, as shown in FIG. 1, or can form substantially the entire energy transfer medium, as shown in FIG. 2. The energy transfer medium 14 and/or the variable viscosity fluid 50 transfer energy from the second member 22 to the first member 18 during use, as described in greater detail below. The variable viscosity fluid or material 50 can be disposed or contained in flexible bags or bladders 54.

Figure 2B:
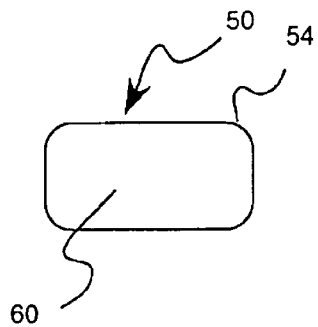
FIGS. 2b–2d are schematic views of an energy transfer medium including a shear stiffening material in accordance with an embodiment of the present invention.
Figure 2C:
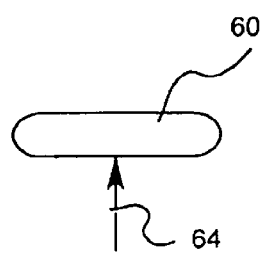
Figure 2D:
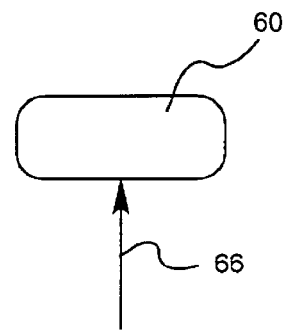

Referring to FIGS. 2b–2d, the variable viscosity fluid or material 50 can include a shear stiffening material 60. Such a shear stiffening material 60 increases in viscosity as a load or strain (or load or strain rate) is applied, or as the load or strain increases. An example of such shear stiffening material is a composition of cornstarch and water. Under little or no load or strain (indicated by arrow 64), the shear stiffening material 60 can be less viscous and capable of greater flow, and thus can be displacable while the energy transfer medium can be compressible, as shown in FIG. 2c. Under greater load or strain (indicated by arrow 66), the shear stiffening material 60 can be more viscous and less capable of flowing, and thus can be less displacable while the energy transfer medium can be less compressible, as shown in FIG. 2d. It will be appreciated that the less-viscous shear stiffening material dissipates more energy or force so that less energy or force is transferred by the material. Similarly, the more-viscous shear stiffening material transfers more energy or force.

Figure 2E:
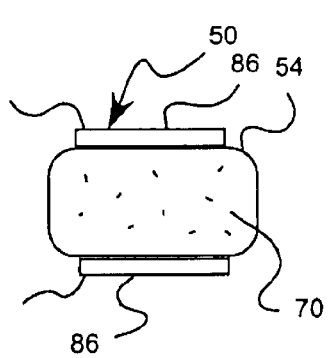
FIGS. 2e–2g are schematic views of an energy transfer medium including an electro rheologic material in accordance with an embodiment of the present invention.
Figure 2F:
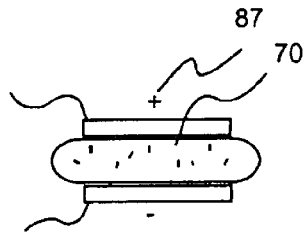
Figure 2G:
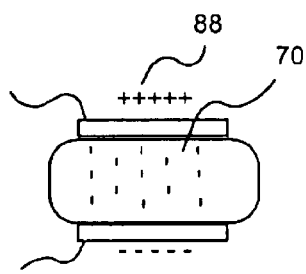

Referring to FIGS. 2e–2g, the variable viscosity fluid or material 50 can include an electro rheologic fluid 70 that is responsive to an applied electric field to alter its viscosity. Such an electro rheologic fluid 70 increases in viscosity as an electric field is applied. Under little or no electric field (indicated at 87), the electro rheologic fluid 70 can be less viscous and capable of greater flow, and thus can be displacable, as shown in FIG. 2f. Under a greater electric field (indicated at 88), the electro rheologic fluid 70 can be more viscous and less capable of flowing, and thus can be less displacable, as shown in FIG. 2g. Again, it will be appreciated that the less-viscous electro rheologic fluid dissipates more energy or force so that less energy or force is transferred by the fluid. Similarly, the more-viscous electro rheologic fluid transfers more energy or force.

Referring again to FIG. 2, the foot device 10 can include a transducer 74, such as a strain gauge, coupled to the first and/or second member 18 and/or 22. The transducer 74 senses strain or deformation in the member 18 and/or 22. The transducer 74 can be operatively coupled to control electronics 78 and a power source 82. The control electronics 78 and transducer 74 can be operatively coupled to the electro rheologic fluid, such as by electrodes 86 (FIG. 2e) coupled to the bag 54. The control electronics 78 can include amplifier circuitry, while the power source 82 can be a battery. The transducer 74 senses deflection or strain in the first and/or second members 18 and 22 and produces a signal that can be sent to the control electronics 78. The control electronics 78 can include amplifier circuitry to amplify the signal to create a control signal. In addition, the control electronics 78 can include circuitry to accept only signals that correspond to a predetermined minimum strain or deflection. The control signal can be applied to the electro rheologic fluid 70 by the electrodes 86 (FIG. 2e). It will be appreciated that the control electronics 78 can include inputs to vary the amplification, minimums, etc., to control or customize the energy transfer of the fluid, and the stiffness of the foot device.

Alternatively, the transducer 74 can be coupled to the energy transfer medium 14, or the bag or bladder 54 containing the variable viscosity fluid 50. Thus, the transducer 74 can be configured to sense pressure of the variable viscosity fluid 50 in the bladder 54. Similarly, the transducer 74 can be configured to sense deflection of the energy transfer medium 14.

Referring to FIGS. 2e–2g, such an electro rheologic fluid 70 can include particles or filings in an oil. As the electric field 88 is applied, the particles or filings align, increasing the viscosity of the fluid 70, or the oil with particles or filings. With no or little electrical field 87, the particles or filings are random, decreasing the viscosity of the fluid 70, or the oil with particles or filings.

Figure 2H:
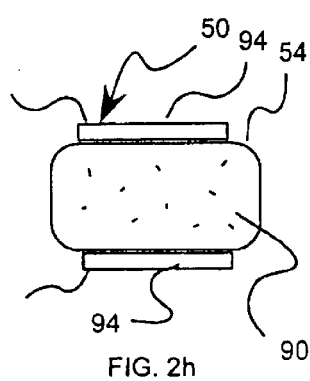
FIGS. 2h–2j are schematic views of an energy transfer medium including a magneto rheologic material in accordance with an embodiment of the present invention.
Figure 2I:
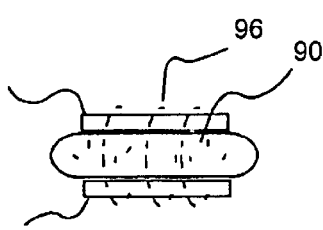
Figure 2J:
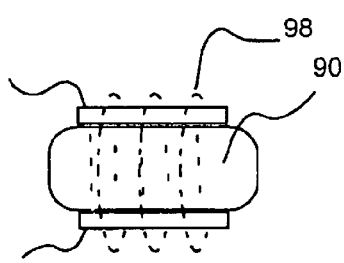

Referring to FIGS. 2h–2j, the variable viscosity fluid or material 50 can include a magneto rheologic fluid 90 that is responsive to an applied magnetic field to alter its viscosity. Such a magneto rheologic fluid 90 increases in viscosity as a magnetic field is applied. Under little or no magnetic field (represented by lines 96), the magneto rheologic fluid 90 can be less viscous and capable of greater flow, and thus can be displacable, as shown in FIG. 2i. Under a greater magnetic field (represented by lines 98), the magneto rheologic fluid 90 can be more viscous and less capable of flowing, and thus can be less displacable, as shown in FIG. 2j. Again, it will be appreciated that the less-viscous magneto rheologic fluid dissipates more energy or force so that less energy or force is transferred by the fluid. Similarly, the more-viscous magneto rheologic fluid transfers more energy or force.

The magnetic field can be applied by magnets 94 that are operatively coupled to the bag 54. The magnets 94 can be electromagnets operatively coupled to the control electronics 78 (FIG. 2) using the control signal to generate the magnetic field. Such a magneto rheologic fluid 90 can include particles or filings in an oil. As the magnetic field 98 is applied, the particles or filings align, increasing the viscosity of the fluid, or the oil with particles or filings. With little or no magnetic field 96, the particles or filings are random, decreasing the viscosity of the fluid, or the oil with particles or filings.

Figure 2K:
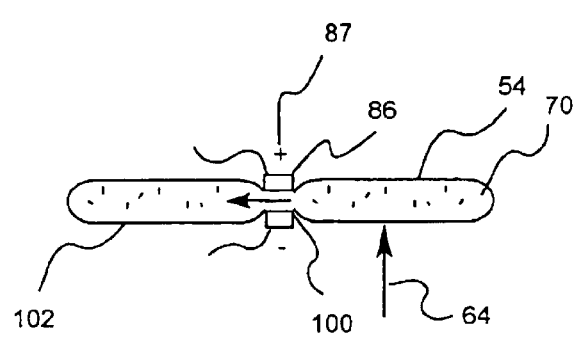
FIGS. 2k and 2l are schematic views of an energy transfer medium including an electro rheologic material in accordance with an embodiment of the present invention.
Figure 2L:
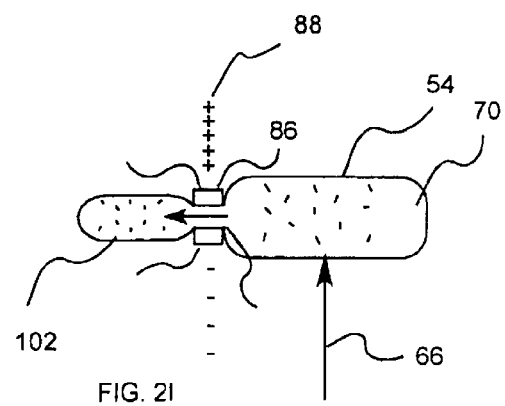

Referring to FIGS. 2k and 2l, the electro rheologic fluid 70 can be forced through, or can pass through, an orifice 100 and into a reservoir 102 under the loading of the foot. The electrodes 86 can be disposed around the orifice 100 to apply and electric field at or near the orifice. The electro rheologic fluid 70 is responsive to the applied electric field to alter its viscosity. Such an electro rheologic fluid 70 increases in viscosity as the electric field is applied, thus impeding the flow of the fluid 70 through the orifice. Under little or no electric field (indicated at 87), the electro rheologic fluid 70 can be less viscous and capable of greater flow, and thus can pass through the orifice 100, as shown in FIG. 2k. Therefore, under lesser force or load 64, the fluid 70 flows through the orifice 100 for less energy transfer, and a softer feel. Under a greater electric field (indicated at 88), the electro rheologic fluid 70 can be more viscous and less capable of flowing, and thus is impeded from flowing through the orifice 100, as shown in FIG. 2l. Therefore, under greater force or load 66, the fluid 70 is impeded from flowing through the orifice 100 for more energy transfer and a stiffer feel.

Figure 2M:
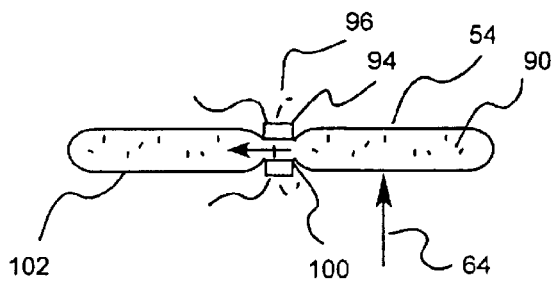
FIGS. 2m and 2n are schematic views of an energy transfer medium including a magneto rheologic material in accordance with an embodiment of the present invention.
Figure 2N:
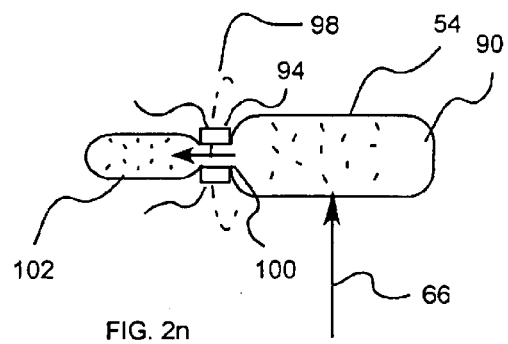

Referring to FIGS. 2m and 2n, the magneto rheologic fluid 90 can be forced through, or can pass through, an orifice 100 and into a reservoir 102 under the loading of the foot. The magnets 94 can be disposed around the orifice 100 to apply a magnetic field at or near the orifice. The magneto rheologic fluid 90 is responsive to the applied magnetic field to alter its viscosity. Such a magneto rheologic fluid 90 increases in viscosity as the magnetic field is applied, thus impeding the flow of the fluid 90 through the orifice. Under little or no magnetic field (indicated at 96), the magneto rheologic fluid 90 can be less viscous and capable of greater flow, and thus can pass through the orifice 100, as shown in FIG. 2m. Therefore, under lesser force or load 64, the fluid 90 flows through the orifice 100 for less energy transfer, and a softer feel. Under a greater magnetic field (indicated at 98), the magneto rheologic fluid 90 can be more viscous and less capable of flowing, and thus is impeded from flowing through the orifice 100, as shown in FIG. 2n. Therefore, under greater force or load 66, the fluid 90 is impeded from flowing through the orifice 100 for more energy transfer and a stiffer feel.

Figure 3A:
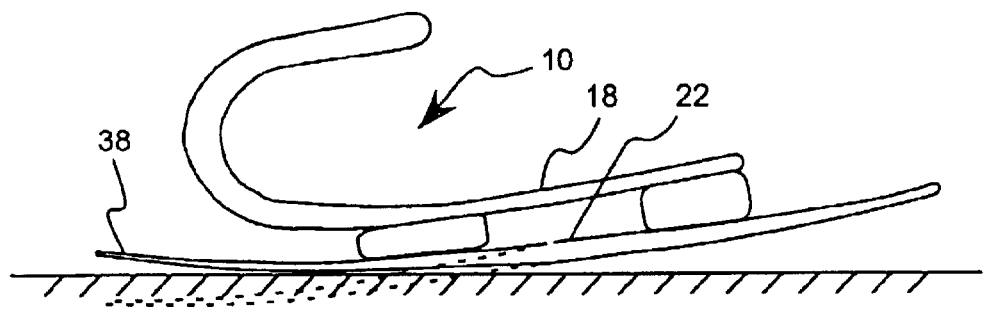
FIGS. 3a–3d are side schematic views of the prosthetic foot of FIG. 2 demonstrating the operation of prosthetic foot.
Figure 3B:
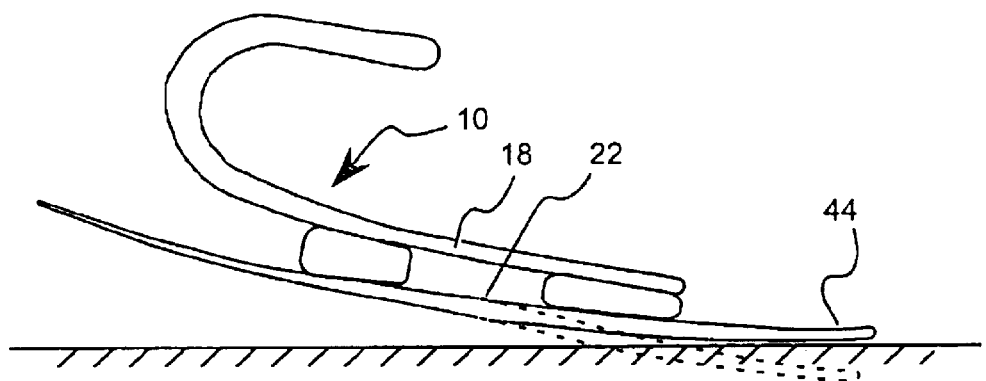
Figure 3C:
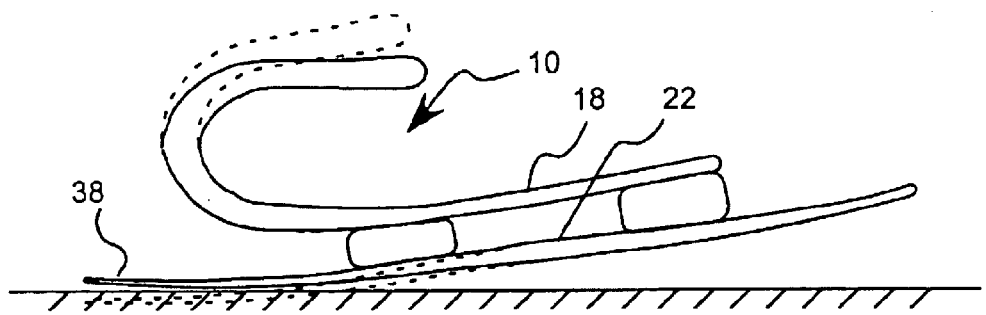
Figure 3D:
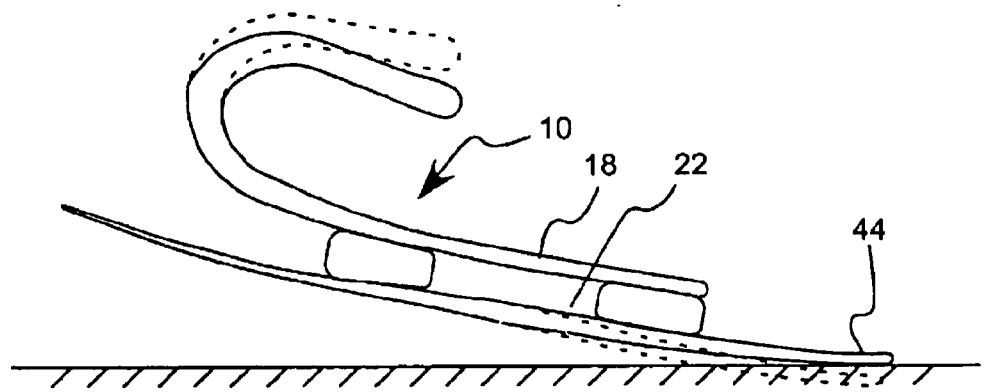

Referring to FIGS. 3a–3d, the operation of the foot device 10 is illustrated, with a lower force application, such as walking, illustrated in FIGS. 3a and 3b, and with a higher force application, such as running, illustrated in FIGS. 3c and 3d. Referring to FIG. 3a, as the user steps on the foot device 10, an applied force, such as the user's weight, causes the heel portion 38 of the second member 22 to deflect (indicated by the solid and dashed lines). The secondary member 22 applies a force to the energy transfer medium 14 and variable viscosity fluid that may be a lesser force due to the operation of the foot device 10 in a walking application. The energy transfer medium 14 compresses to a greater extent, dissipating some of the force, and transferring less force to the first member 18. Thus, the energy transfer medium 14 or variable viscosity fluid allows the second member 22 or heel portion 38 to deflect and/or move with respect to the first member 18, providing a soft, cushioned feel.

Referring to FIG. 3b, as the user continues to step, or walk, on the foot device 10, the toe portion 44 of the second member 22 deflects (indicated by the solid and dashed lines). Again, the secondary member 22 applies a force to the energy transfer medium 14 and variable viscosity fluid that may be a lesser force due to the operation of the foot device 10 in a walking application. The energy transfer medium 14 compresses to a greater extend, dissipating some of the force, and transferring less force to the first member 18. Again, the energy transfer medium 14 or variable viscosity fluid allows the second member 22 or toe portion 44 to deflect and/or move with respect to the first member 18, providing a soft, cushioned feel.

Referring to FIG. 3c, as the user exerts a greater force on the foot device 10, such as by running, the heel portion 38 of the second member 22 deflects (indicated by the solid and dashed lines). The secondary member 22 applies a force to the energy transfer medium 14 and variable viscosity fluid that may be a greater force due to the operation of the foot device 10 in a running application. The energy transfer medium 14 and variable viscosity fluid dissipate less or no force, and transfers more or all of the force to the first member 18. As described above, the variable viscosity fluid can be a shear stiffening material that increases viscosity due to the applied load or strain. Or the variable viscosity fluid can be a magneto or electro rheologic fluid that increases viscosity due to the application of a magnetic or electric field corresponding to the strain or deflection sensed by the transducer. Thus, the energy transfer medium 14 or variable viscosity fluid transfers the energy or force from the second member 22 to the first member 18 causing the first member 18 to deflect, indicated by the dashed and solid lines. Therefore, in a higher load application, or running, both the first and second members 18 and 22 can be more fully utilized.

Referring to FIG. 3d, as the user continues to run on the foot device 10, the toe portion 44 of the second member 22 deflects (indicated by the solid and dashed lines). The secondary member 22 applies a force to the energy transfer medium 14 and variable viscosity fluid that may be a greater force due to the operation of the foot device 10 in a running application. The energy transfer medium 14 and variable viscosity fluid transfer more force to the first member 18 causing the first member 18 to deflect (indicated by the dashed and solid lines). Again, in a higher load application, both the first and second members 18 and 22 can be more fully utilized.

Because the first and second members 18 and 22 can be made of a resilient material, the members 18 and 22 act as springs and store the energy to be subsequently released. As the user lifts the foot 10, the toe portion 44 of the foot 10 returns to its original position, pushing-off.

Figure 4:
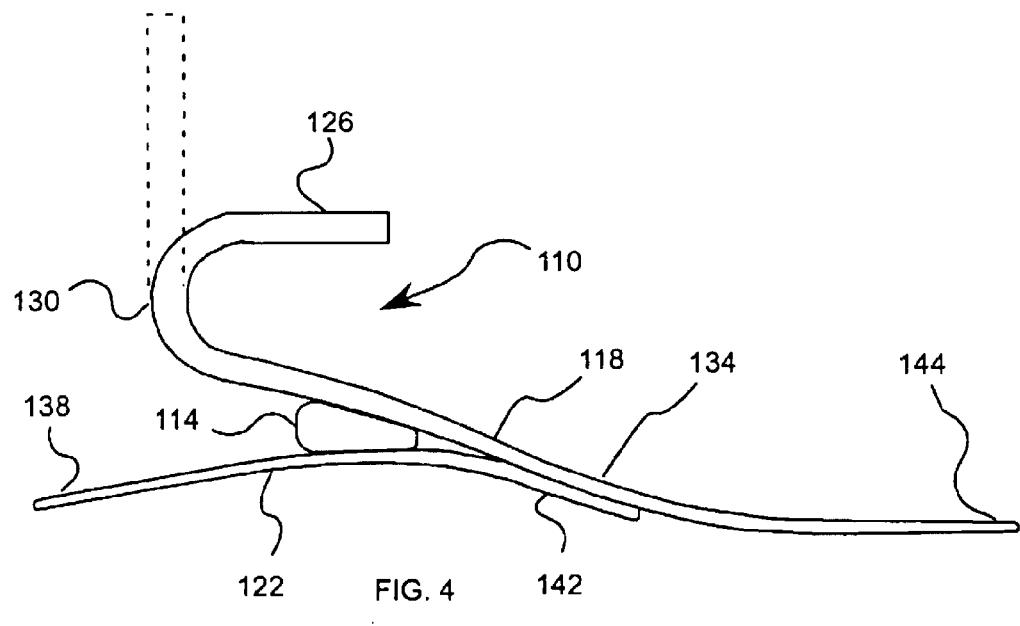
FIG. 4 is a side view of another prosthetic foot having an energy transfer medium with variable viscosity fluid in accordance with another embodiment of the present invention.

Referring to FIG. 4, another prosthetic foot device 110 is shown with an energy transfer medium 114. The energy transfer medium 114 can be similar to that described above, including a variable viscosity fluid or material. The foot device 110, however, has first and second members 118 and 122 with a different configuration than that described above. The first member 118 can be an upper or forefoot member with an attachment section 126 (horizontal shown in solid lines, vertical shown in dashed lines), curving downwardly and forwardly through a curvilinear spring or ankle section 130, an arch section 134, and a toe section 144 at a toe location of toes of a natural foot. Thus, the first member 118 can have a general C-shape or a J-shape. The second member 122 can be a lower heel member and can have an attachment section 142 attached to the arch section 134 of the first member 118, and extending rearwardly towards a heel section 138 at a heel location of a natural heel. The energy transfer medium 114 can be disposed between the first and second members 118 and 122, and can operate as described above.

Figure 5:
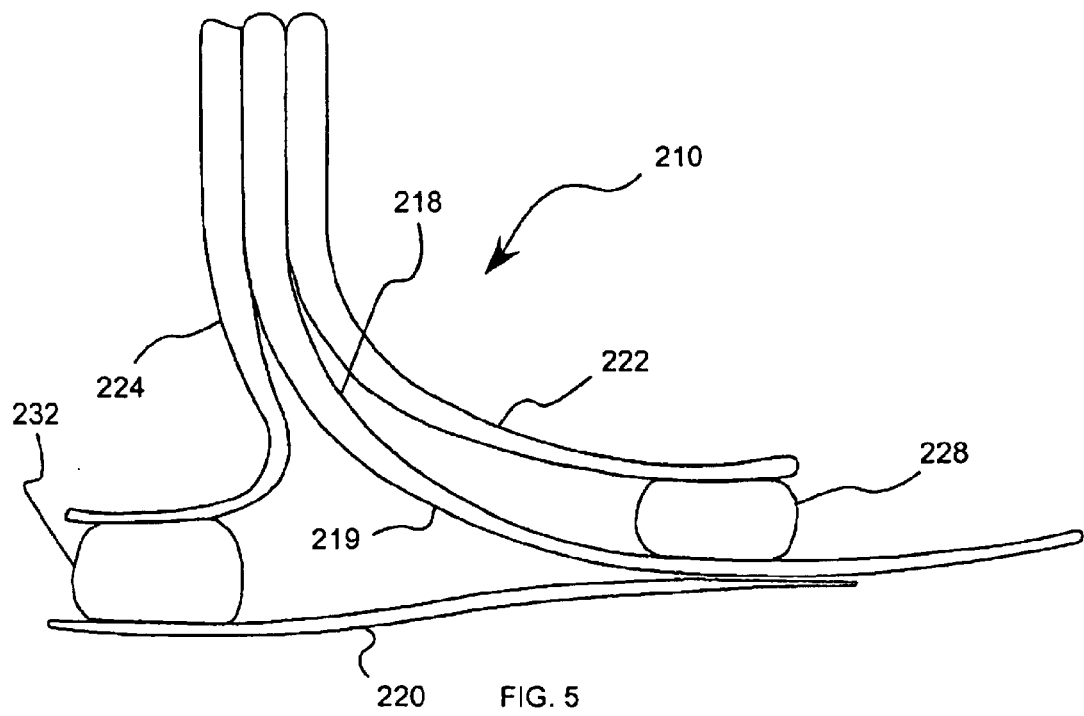
FIG. 5 is a side view of another prosthetic foot having an energy transfer medium with variable viscosity fluid in accordance with another embodiment of the present invention.

Referring to FIG. 5, another prosthetic foot device 210 is shown which is similar in many respects to the foot device 110 shown in FIG. 4 and described above. The foot device 210 can include a first member 218 that can include both 1) an upper forefoot member 219, and 2) a lower heel member 220, as described above. In addition, the foot device 210 can include a second member that can be a forefoot and/or heel reinforcement member 222 and/or 224. The forefoot reinforcement member 224 can have an attachment section attached to the first member 218 or socket, and extend downwardly and forwardly in a curvilinear fashion above the upper forefoot member 219 of the first member 218. A forefoot energy transfer medium 228 can be disposed between the first and second members 218 and 222, or between the upper forefoot member 219 and the forefoot reinforcement member 222. Similarly, the lower heel reinforcement member 224 can include an attachment section attached to the first member 218 or socket, and extend downwardly and rearwardly in a curvilinear fashion above the lower heel member 220 of the first member 218. A heel energy transfer medium 232 can be disposed between the first and second members 218 and 224, or between the lower heel member 220 and the heel reinforcement member 224.

Figure 6A:
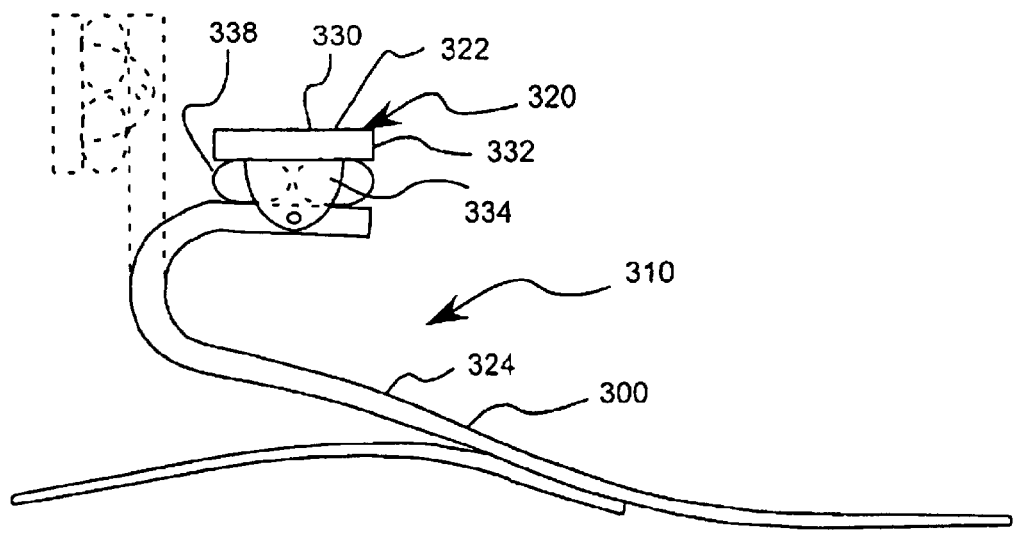
FIG. 6a is a side view of another prosthetic foot having an energy transfer medium with variable viscosity fluid in accordance with another embodiment of the present invention.
Figure 6B:
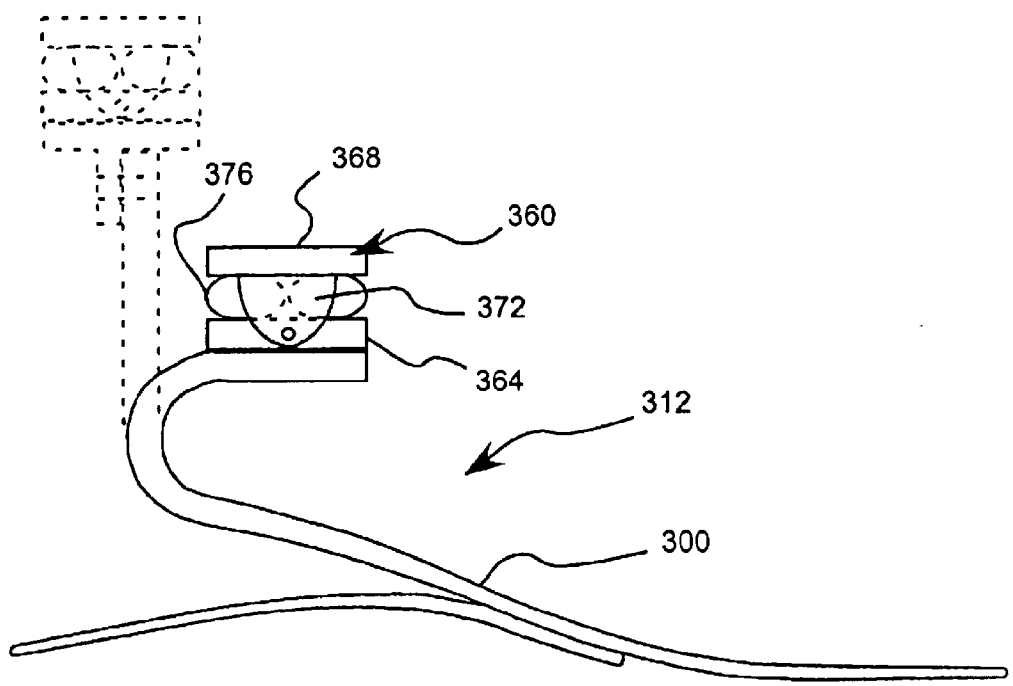
FIG. 6b is a side view of another prosthetic foot having an energy transfer medium with variable viscosity fluid in accordance with another embodiment of the present invention.

Referring to FIGS. 6a and 6b, a prosthetic foot 300 is shown with adaptors to convert the prosthetic foot 300 into a prosthetic foot device 310 and 312 with a variable energy transfer medium. The prosthetic foot 300 shown in FIGS. 6 and 7 is similar to the prosthetic foot device shown in FIG. 4 and described above. It will be appreciated, however, that the adaptors can be used with various different configurations, such as those shown in FIGS. 2 and 5.

Referring to FIG. 6a, an adaptor 320 is coupled to the prosthetic foot 300 such that the adaptor 320 forms a first member 322, and the prosthetic foot 300 forms the second member 324. The adaptor 320 can attach in a horizontal manner to a horizontal attachment section of the prosthetic foot, as shown in solid lines, or in a vertical manner to a vertical attachment section of the prosthetic foot, as show in dashed lines. (It will of course be appreciated that the adaptor can be attached at any angle, and the horizontal and vertical are shown as typical attachments.)

The adaptor 320 can include a bracket 330 pivotally coupled to the foot 300 or attachment section. The bracket 330 can include a base 332 and a pair of arms 334 extending therefrom with distal ends pivotally coupled to the foot 300. An energy transfer medium 338 similar to those described above with a variable viscosity fluid or material can be disposed between the first member 322 or adaptor 320 and the second member 324 or foot 300. Therefore, the adaptor 320 advantageously adds the energy transfer medium 338 to the prosthetic foot 300.

Referring to FIG. 6b, an adaptor 360 is shown that is similar to the adaptor shown in FIG. 6a, and described above. The adaptor 360 further includes an attachment plate 364 for attachment to the foot 300. The adaptor 360 can include a similar base 368 with arms 372 extending therefrom and pivotally attached to the attachment plate 364. An energy transfer medium 376 is disposed between the base 368 and the attachment plate 364. Thus, the adaptor 360 can be coupled to the foot without having a pivotal attachment directly on the foot itself.

Referring to FIGS. 6c and 6d, an adaptor 400 is shown that is similar in many respects to the adaptors described above. The adaptor 400 advantageously can allow the foot or members to pivot in both 1) a longitudinal (or forward and rearward) direction, and 2) a lateral direction. The adaptor 400 can include an attachment plate 402 for attachment to the foot, similar to that described above. The adaptor can include a base 404 that is coupled to the attachment plate 402, such is by a pin, so that the base 404 and the attachment member 402 can pivot with respect to one another. An energy transfer medium 408, similar to those described above, can be disposed between the base 404 and the attachment plate 402. The energy transfer medium 408 can be disposed in various configurations, including in longitudinal and lateral alignment, as shown FIG. 6c, or in opposite corners, as shown in FIG. 6d.

Referring to FIG. 7, another prosthetic foot device 410 is shown with an energy transfer medium 414. The energy transfer medium 414 can be similar to that described above, including a variable viscosity fluid or material. The foot device 410 also includes first and second members 418 and 422 with a different configuration than that described above. The first member 418 can be an upper attachment member with an attachment section 426 for coupling to a stump of an amputee. The second member 422 can include a lower foot member with an attachment section 440 curving both 1) downwardly and forwardly to a toe section 444 at a toe location of toes of a natural foot, and 2) downwardly and rearwardly to a heel section 438 at a heel location of a natural heel. The second member 422 can be pivotally attached to the first member 418, such as with a pivot pin 450. The energy transfer medium 414 can be disposed between the first and second members 418 and 422, and can operate as described above.

In use, the second member 440 can pivot about the pivot pin 450 with respect to the first member 418. The energy transfer medium 414 can include a variable viscosity fluid as described above to adjust the feel or softness of the foot.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed is:

1. A prosthetic foot device with variable stiffness response, the device comprising:

a) first and second foot members, configured to be coupled to an amputee, at least one of the first and second foot members being configured to be coupled to an amputee, and at least one of the first and second foot members being a resilient member capable of storing energy during deflection; and b) a variable energy transfer medium, disposed between the first and second members, to transfer at least some energy between the first and second members during use; and c) the energy transfer medium including a flexible bladder with a variable viscosity fluid such that the variable viscosity fluid, and thus the energy transfer medium, variably transfers energy between the first and second members to vary stiffness of the prosthetic foot device.

2. A device in accordance with claim 1, wherein the variable viscosity fluid includes a shear stiffening material that increases in viscosity with an increase in a load factor applied to the shear stiffening material.

3. A device in accordance with claim 2, wherein the load factor includes at least one load factor selected from the group consisting of: a load, a load rate, a strain, a strain rate, a pressure, or a deflection.

4. A device in accordance with claim 1, wherein the variable viscosity fluid includes at least one fluid selected from the group consisting of: a magneto rheologic fluid responsive to a magnetic field, or an electro rheologic fluid responsive to an electric field.

5. A device in accordance with claim 4, further comprising:
    a transducer, coupled to the prosthetic foot device, to sense a load factor;
    a power source, coupled to the transducer;
    control electronics, coupled to the transducer and the variable viscosity fluid, to apply an electric or magnetic field in response to the load factor sensed by the transducer.

6. A device in accordance with claim 4, further comprising: an orifice through which the variable viscosity fluid flows during use.

7. A device in accordance with claim 1, wherein:
    the first member includes an upper member having an attachment section configured to be coupled to a socket, and extending downwardly therefrom; and
    the second member includes a lower foot member having a heel section disposed at a natural location of a heel of a user, and a toe section disposed at a natural location of a toe of the user.

8. A device in accordance with claim 1, wherein:
    the first member includes an upper forefoot member having an attachment section configured to be coupled to a socket, and extending downwardly therefrom; and
    the second member includes a lower heel member having a heel section disposed at a natural location of a heel of a user, and an attachment section attached to the upper forefoot member.

9. A device in accordance with claim 1, wherein:
    the first member includes:
        an upper forefoot member having an attachment section configured to be coupled to a socket, and extending downwardly therefrom; and
        a lower heel member having a heel section disposed at a natural location of a heel of a user, and an attachment section attached to the upper forefoot member; and
    the second member includes a forefoot reinforcement member, disposed above the upper forefoot member.

10. A device in accordance with claim 1, wherein:
    the first member includes:
        an upper forefoot member having an attachment section configured to be coupled to a socket, and extending downwardly therefrom; and
        a lower heel member having a heel section disposed at a natural location of a heel of a user, and an attachment section attached to the upper forefoot member; and
    the second member includes a heel reinforcement member, disposed above the lower heel member.

11. A device in accordance with claim 1, wherein:
    the first member includes an adaptor, configured to be coupled to a socket; and
    the second member includes at least an upper member having an attachment section attached to the adaptor and configured to be coupled to the socket by the adaptor, and extending downwardly therefrom.

* * * * *